US008725425B2

(12) United States Patent
Heiner et al.

(10) Patent No.: US 8,725,425 B2
(45) Date of Patent: May 13, 2014

(54) IMAGE DATA EFFICIENT GENETIC SEQUENCING METHOD AND SYSTEM

(75) Inventors: David L. Heiner, San Diego, CA (US); Robert C. Kain, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 663 days.

(21) Appl. No.: 12/020,739

(22) Filed: Jan. 28, 2008

(65) Prior Publication Data

US 2008/0182757 A1 Jul. 31, 2008

Related U.S. Application Data

(60) Provisional application No. 60/897,646, filed on Jan. 26, 2007, provisional application No. 60/897,647, filed on Jan. 26, 2007.

(51) Int. Cl.
| | | |
|---|---|---|
| *G06F 19/00* | (2011.01) | |
| *G06F 15/00* | (2006.01) | |
| *C12Q 1/68* | (2006.01) | |
| *C12M 1/00* | (2006.01) | |

(52) U.S. Cl.
USPC ............... 702/20; 700/1; 435/6.1; 435/283.1

(58) Field of Classification Search
None
See application file for complete search history.

(56) References Cited

U.S. PATENT DOCUMENTS

| | | | |
|---|---|---|---|
| 4,042,338 | A | 8/1977 | Huber |
| 5,202,418 | A | 4/1993 | Lebl et al. |
| 5,338,831 | A | 8/1994 | Lebl et al. |
| 5,342,585 | A | 8/1994 | Lebl et al. |
| 5,367,401 | A | 11/1994 | Saulietis |
| 5,386,567 | A | 1/1995 | Lien et al. |
| 5,434,083 | A | 7/1995 | Mitsumaki et al. |
| 5,601,141 | A | 2/1997 | Gordon et al. |
| 5,614,608 | A | 3/1997 | Krchnak et al. |
| 6,045,760 | A | 4/2000 | Aizawa et al. |
| 6,078,390 | A | 6/2000 | Bengtsson |
| 6,121,054 | A | 9/2000 | Lebl |
| 6,130,046 | A | 10/2000 | Hubbell et al. |
| 6,264,891 | B1 | 7/2001 | Heyneker et al. |
| 6,335,166 | B1 | 1/2002 | Ammann et al. |
| 6,663,832 | B2 | 12/2003 | Lebl et al. |
| 6,839,454 | B1 | 1/2005 | Park |
| 6,846,460 | B1 | 1/2005 | Lebl |
| 2002/0044894 | A1 | 4/2002 | Lebl et al. |
| 2003/0044781 | A1 | 3/2003 | Korlach et al. |
| 2003/0196695 | A1 * | 10/2003 | O'Connor et al. ......... 137/87.01 |
| 2004/0219063 | A1 | 11/2004 | Heiner et al. |
| 2006/0083428 | A1 | 4/2006 | Ghosh et al. |
| 2006/0293558 | A1 | 12/2006 | De Groen et al. |
| 2007/0114362 | A1 | 5/2007 | Feng et al. |
| 2007/0117178 | A1 | 5/2007 | Heiner et al. |
| 2008/0003571 | A1 * | 1/2008 | McKernan et al. ............... 435/6 |
| 2009/0155793 | A1 | 6/2009 | Oliphant |

FOREIGN PATENT DOCUMENTS

| | | |
|---|---|---|
| EP | 0445915 A1 | 1/1991 |
| WO | WO 99/08233 A | 2/1999 |
| WO | 00/18957 | 6/2000 |
| WO | 00/44491 A2 | 8/2000 |
| WO | 02/04123 A1 | 1/2002 |
| WO | 02/16040 A1 | 2/2002 |
| WO | 2006/064199 A1 | 6/2006 |
| WO | 2006/113931 A1 | 10/2006 |
| WO | 2007/123744 A2 | 11/2007 |

OTHER PUBLICATIONS

Shendure et al. Accurate Multiplex Polony Sequencing of an Evolved Bacterial Genome Science vol. 309, pp. 1728-1732 and Supplemental Material (2005).*
Klincewicz Hub location in backbone/tributary network design: a review Location Science vol. 6, pp. 307-335 (1998).*
Rahnenfuhrer et al. Hybrid clustering for microarray image analysis combining intensity and shape features BMC Bioinformatics vol. 5, article 47 (2004).*
Jianping Hua et al., "Microarray BASICA: background adjustment, segmentation, image compression and analysis of microarray images," EURASIP Journal on Applied Signal Processing, vol. 2004, No. 1, Jan. 1, 2004, pp. 92-107.
Luo et al., "Storage and Transmission of Microarray Images," Drug Discovery Today, vol. 10, No. 23-24, Dec. 1, 2005; pp. 1689-1695.
Adjeroh et al., "On denoising and compression of DNA microarray images," Pattern Recognition, vol. 39, No. 12, Dec. 1, 2006, pp. 2478-2493.
Marcel Margulies, et al.; "Genome sequencing in microfabricated high-density picolitre reactors;" Nature, vol. 437, No. 15, pp. 376-380, Sep. 15, 2005; Corrigenda from Nature, vol. 441, May 4, 2006.
Metzker, M. L.; "Emerging Technologies in DNA Sequencing", Genome Research, Cold Spring Harbor Laboratory Press, Dec. 1, 2005, pp. 1767-1776, vol. 15, No. 12, Woodbury, NY, USA.

(Continued)

*Primary Examiner* — John S Brusca
(74) *Attorney, Agent, or Firm* — Fletcher Yoder P.C.

(57) ABSTRACT

A technique is disclosed for performing sequencing of polymers such as DNA and RNA. A sample containing multiple sites to be sequenced is cyclically subjected to attachment of nucleotides, and imaging. A digital mask corresponding to sites of interest in the sample array is generated and image data for the sites is processed differently from image data not corresponding to sites of interest. The latter may be discarded during the sequencing operation. The use of the mask improves computational efficiency and reduces memory allocated for the image data during sequencing.

30 Claims, 8 Drawing Sheets

(56) References Cited

OTHER PUBLICATIONS

Gharizadeh, B., et al; "Methodological Improvements of Pyrosequencing Technology", Journal of BioTechnology, Jul. 25, 2006, pp. 504-511, vol. 124, No. 3, Amsterdam, NL, Elsevier Science Publishers.

Marra, Marco A., et al., High-throughput plasmid DNA purification for 3 cents per sample, Nucleic Acids Research, 1999, vol. 27, No. 24, 1999 Oxford University Press.

Margulies, Marcel., et al., Genome sequencing in microfabricated high-density picolitre reactors (abstract), Nature 437, pp. 376-380, Sep. 15, 2005, and Supplemental Content Figures 1-11, Tables 1-4, and Materials and Methods pp. 1-34 (2005).

* cited by examiner

500
IMAGE DATA EFFICIENT GENETIC SEQUENCING METHOD AND SYSTEM

CROSS REFERENCE TO RELATED APPLICATIONS

This application claims priority of U.S. Provisional Patent Application No. 60/897,646, entitled "Image Data Efficient Genetic Sequencing Method and System," filed Jan. 26, 2007, which is herein incorporated in its entirety by reference, and of U.S. Provisional Patent Application No. 60/897,647, entitled "Nucleic Acid Sequencing System and Method," filed Jan. 26, 2007, which is herein incorporated in its entirety by reference.

BACKGROUND

The present invention relates generally to the field of genetic sequencing. More particularly, the invention relates to improved techniques for permitting automating sequencing of genetic materials by use of arrays of genetic fragments.

Genetic sequencing has become an increasingly important area of genetic research, promising future uses in diagnostic and other applications. In general, genetic sequencing consists of determining the order of nucleotides for a nucleic acid such as a fragment of RNA or DNA. Relatively short sequences are typically analyzed, and the resulting sequence information may be used in various bioinformatics methods to logically fit fragments together so as to reliably determine the sequence of much more extensive lengths of genetic material from which the fragments were derived. Automated, computer-based examination of characteristic fragments have been developed, and have been used more recently in genome mapping, identification of genes and their function, and so forth. However, existing techniques are highly time-intensive, and resulting genomic information is accordingly extremely costly.

A number of alternative sequencing techniques are presently under investigation and development. These include the use of microarrays of genetic material that can be manipulated so as to permit parallel detection of the ordering of nucleotides in a multitude of fragments of genetic material. The arrays typically include many sites formed or disposed on a substrate. Additional materials, typically single nucleotides or strands of nucleotides (oligonucleotides) are introduced and permitted or encouraged to bind to the template of genetic material to be sequenced. Sequence information may then be gathered by imaging the sites. In certain current techniques, for example, each nucleotide type is tagged with a fluorescent tag or dye that permits analysis of the nucleotide attached at a particular site to be determined by analysis of image data.

Although such techniques show promise for significantly improving throughput and reducing the cost of sequencing, further progress in speed, reliability and efficiency of data handling is needed.

For example, in certain sequencing approaches that use image data to evaluate individual sites, large volumes of image data may be produced during sequential cycles of sequencing. In systems relying upon sequencing by synthesis (SBS), for example, dozens of cycles may be employed for sequentially attaching nucleotides to individual sites. Images formed at each step result in a vast quantity of digital data representative of pixels in high-resolution images. These images are analyzed to determine what nucleotides have been added to each site at each cycle of the process. Other images may be employed to verify de-blocking and similar steps in the operations.

The image data is important for determining the proper sequence data for each individual site. However, the quantity of image data will become unwieldy as systems become capable of more rapid and large-scale sequencing. There is need, therefore, for improved techniques in the management of such data during and after the sequencing process.

BRIEF DESCRIPTION

The present invention provides a significantly improved technique for performing image-based sequencing, particularly for embodiments using arrays of nucleic acids arranged in sites on a substrate. The technique may be employed with any number of different sequencing approaches, such as sequencing by synthesis (SBS), sequencing by ligation, and so forth. In general, the technique relies upon the creation of a mask after identification of locations of particular sites of interest on the substrate. The mask may conveniently be defined as a binary mask in which the sites of interest, on a pixilated basis, are attributed first value, and other locations on the array are attributed a different value. This mask may be generated prior to sequencing, or after or during a first cycle of sequencing. Some of the sites of interest may be control sites, such that the progress of sequencing, and the anticipated results can be analyzed.

Based upon the mask, vast amounts of image data not useful for sequencing may be processed differently from that information which does provide useful sequencing data. The masked areas that do not correspond to sites of interest may be disregarded, and the corresponding image data either simply handled differently (not filtered or analyzed) or may be discarded (e.g., deleted). Because this preferential treatment of the data may occur during sequencing, the overall amount of image data processed and stored by the systems may be greatly reduced, thereby improving computational efficiency and utilizing less memory space both during and after data acquisition.

Accordingly, the invention provides a method for sequencing a plurality of nucleic acids, including the steps of (a) performing a cycle of a sequencing procedure for an array comprising a plurality of nucleic acids at sites of interest; (b) imaging the array to generate image data; (c) analyzing the image data to identify locations of the sites of interest; (d) generating a mask based upon the locations of the sites of interest; and (e) processing the image data based upon the mask to derive sequence data from the image data, the sequence data indicative of nucleotide species present at the sites of interest.

Also provided is a sequencing system, including (a) a camera configured to capture a first image of an array and a second image of the array, wherein the array comprises a plurality of nucleic acids at sites of interest; (b) a computer having instructions for processing the first image of the array to create a mask, wherein the mask preferentially selects signals from the sites of interest; and (c) a data compression device configured to convert the second image to a compressed data packet based on the mask, wherein the compressed data packet comprises signals from the sites of interest, wherein the computer is further configured to process the signals from the sites of interest in the compressed data packet to derive sequence data for the nucleic acids at the sites of interest.

Further provided is a method for sequencing a plurality of nucleic acids, including the steps of (a) performing a cycle of a sequencing procedure for an array comprising a plurality of nucleic acids via a system capable of determining nucleotide sequence of the array; (b) evaluating a parameter of the system indicative of system performance; (c) altering the sequencing procedure for the array based on the parameter; (d) imaging the array to generate image data; (e) analyzing the image data to identify locations of the sites of interest; (f) generating a mask based upon the locations of the sites of interest; and (g) processing the image data based upon the mask to derive sequence data from the image data, the sequence data indicative of nucleotide species present at the sites of interest.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
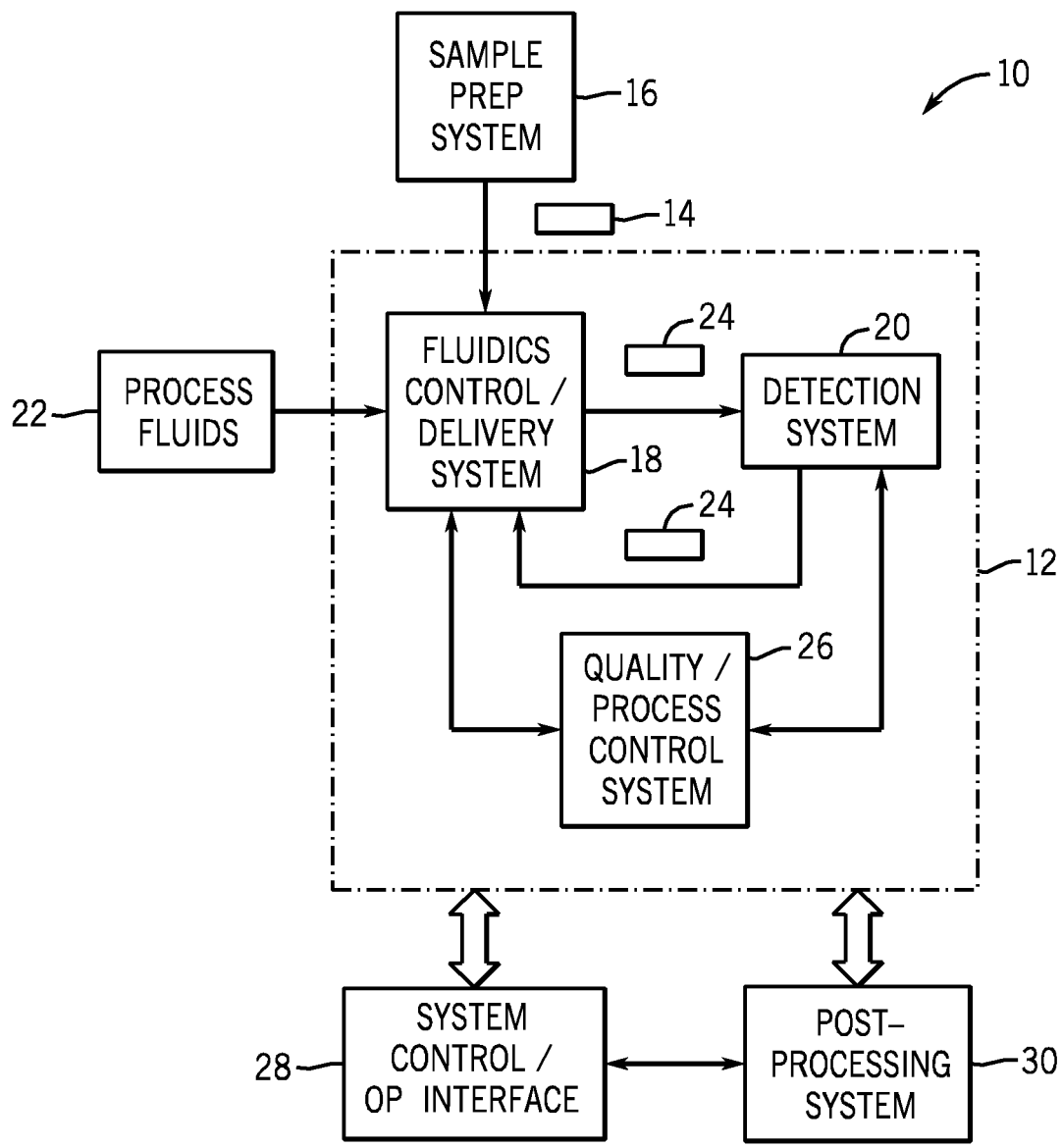
FIG. 1 is a diagrammatical overview of a sequencing system incorporating aspects of the present technique.

Turning now to the drawings, referring first to FIG. 1, a diagrammatical representation of a sequencing system 10 is illustrated as including a sequencer 12 designed to determine sequences of genetic material of a sample 14. The sequencer may function in a variety of manners, and based upon a variety of techniques, including sequencing by primer extension using labeled nucleotides, as in a presently contemplated embodiment, as well as other sequencing techniques such as sequencing by ligation or pyrosequencing. In general, and as described in greater detail below, the sequencer 12 progressively moves samples through reaction cycles and imaging cycles to progressively build oligonucleotides by binding nucleotides to templates at individual sites on the sample. In a typical arrangement, the sample will be prepared by a sample preparation system 16. This process may include amplification of fragments of DNA or RNA on a support to create a multitude of sites of DNA or RNA fragments the sequence of which are determined by the sequencing process. Exemplary methods for producing sites of amplified nucleic acids suitable for sequencing include, but are not limited to, rolling circle amplification (RCA) (Lizardi et al., *Nat. Genet.* 19:225-232 (1998)), bridge PCR (Adams and Kron, *Method for Performing Amplification of Nucleic Acid with Two Primers Bound to a Single Solid Support*, Mosaic Technologies, Inc. (Winter Hill, Mass.); Whitehead Institute for Biomedical Research, Cambridge, Mass., (1997); Adessi et al., *Nucl. Acids Res.* 28:E87 (2000); Pemov et al., *Nucl. Acids Res.* 33:e11(2005); or U.S. Pat. No. 5,641,658), polony generation (Mitra et al., *Proc. Natl. Acad. Sci. USA* 100:5926-5931 (2003); Mitra et al., *Anal. Biochem.* 320:55-65(2003)), or clonal amplification on beads using emulsions (Dressman et al., *Proc. Natl. Acad. Sci. USA* 100:8817-8822 (2003)) or ligation to bead-based adapter libraries (Brenner et al., *Nat. Biotechnol.* 18:630-634 (2000); Brenner et al., *Proc. Natl. Acad. Sci. USA* 97:1665-1670 (2000)); Reinartz, et al., *Brief Funct. Genomic Proteomic* 1:95-104 (2002)). The sample preparation system 16 will typically dispose the sample, which may be in the form of an array of sites, in a sample container for processing and imaging.

The sequencer 12 includes a fluidics control/delivery system 18 and a detection system 20. The fluidics control/delivery system 18 will receive a plurality of process fluids as indicated generally by reference numeral 22, for circulation through the sample containers of the samples in process, designated generally by reference numeral 24. As will be appreciated by those skilled in the art, the process fluids will vary depending upon the particular stage of sequencing. For example, in SBS using labeled nucleotides, the process fluids introduced to the sample will include a polymerase and tagged nucleotides of the four common DNA types, each nucleotide having a unique fluorescent tag and a blocking agent linked to it. The fluorescent tag allows the detection system 20 to detect which nucleotides were last added to probes hybridized to template nucleic acids at individual sites in the array, and the blocking agent prevents addition of more than one nucleotide per cycle at each site. In other processes, such as sequencing by ligation, the process fluids at this stage will include query probes with unique fluorescent tags attached thereto. Similarly, the query probes will bind to the templates at each site in a configuration that allows ligation of the query probes to an anchor primer and may be detected by the detection system 20 for sequencing of the templates at each site.

At other phases of the sequencing cycles, the process fluids 22 will include other fluids and reagents such as reagents for removing extension blocks from nucleotides, cleaving nucleotide linkers, or for removing bases from ligated oligonucleotides to release a newly extendable probe terminus. For example, once reactions have taken place at individual sites in the array of the samples, the initial process fluid containing the tagged nucleotides will be washed from the sample in one or more flushing operations. The sample may then undergo detection, such as by the optical imaging at the detection system 20. Subsequently, reagents will be added by the fluidics control/delivery system 18 to de-block the last added nucleotide and remove the fluorescent tag from each. The fluidics control/delivery system 18 will typically then again wash the sample, which is then prepared for a subsequent cycle of sequencing. Exemplary fluidic and detection configurations that can be used in the methods and devices set forth herein are described in WO 07/123744. In general, such sequencing may continue until the quality of data derived from sequencing degrades due to cumulative loss of yield or until a predetermined number of cycles have been completed, as described in greater detail below.

The quality of samples 24 in process as well as the quality of the data derived by the system, and the various parameters used for processing the samples is controlled by a quality/process control system 26. The quality/process control system 26 will typically include one or more programmed processors, or general purpose or application-specific computers which communicate with sensors and other processing systems within the fluidics control/delivery system 18 and the detection system 20. A number of process parameters may be used for sophisticated quality and process control.

The sequencer 12 also communicates with a system control/operator interface 28 and ultimately with a post-processing system 30. Here again, the system control/operator interface 28 will typically include a general purpose or application-specific computer designed to monitor process parameters, acquired data, system settings, and so forth. The operator interface may be generated by a program executed locally or by programs executed within the sequencer 12. In general, these may provide visual indications of the health of the systems or subsystems of the sequencer, the quality of the data acquired, and so forth. The system control/operator interface 28 may also permit human operators to interface with the system to regulate operation, initiate and interrupt sequencing, and any other interactions that may be desired with the system hardware or software. The post-processing system 30 will typically also include one or more programmed computers that receive detected information, which may be in the form of pixilated image data and derive sequence data from the image data. The post-processing system 30 may include image recognition algorithms which distinguish between colors of dyes attached to nucleotides that bind at individual sites as sequencing progresses (e.g., by analysis of the image data encoding specific colors or intensities), and logs the sequence of the nucleotides at the individual site locations. Progressively, then, the post-processing system 30 will build sequence lists for the individual sites of the sample array which can be further processed to establish genetic information for extended lengths of material by various bioinformatics algorithms.

Figure 2:
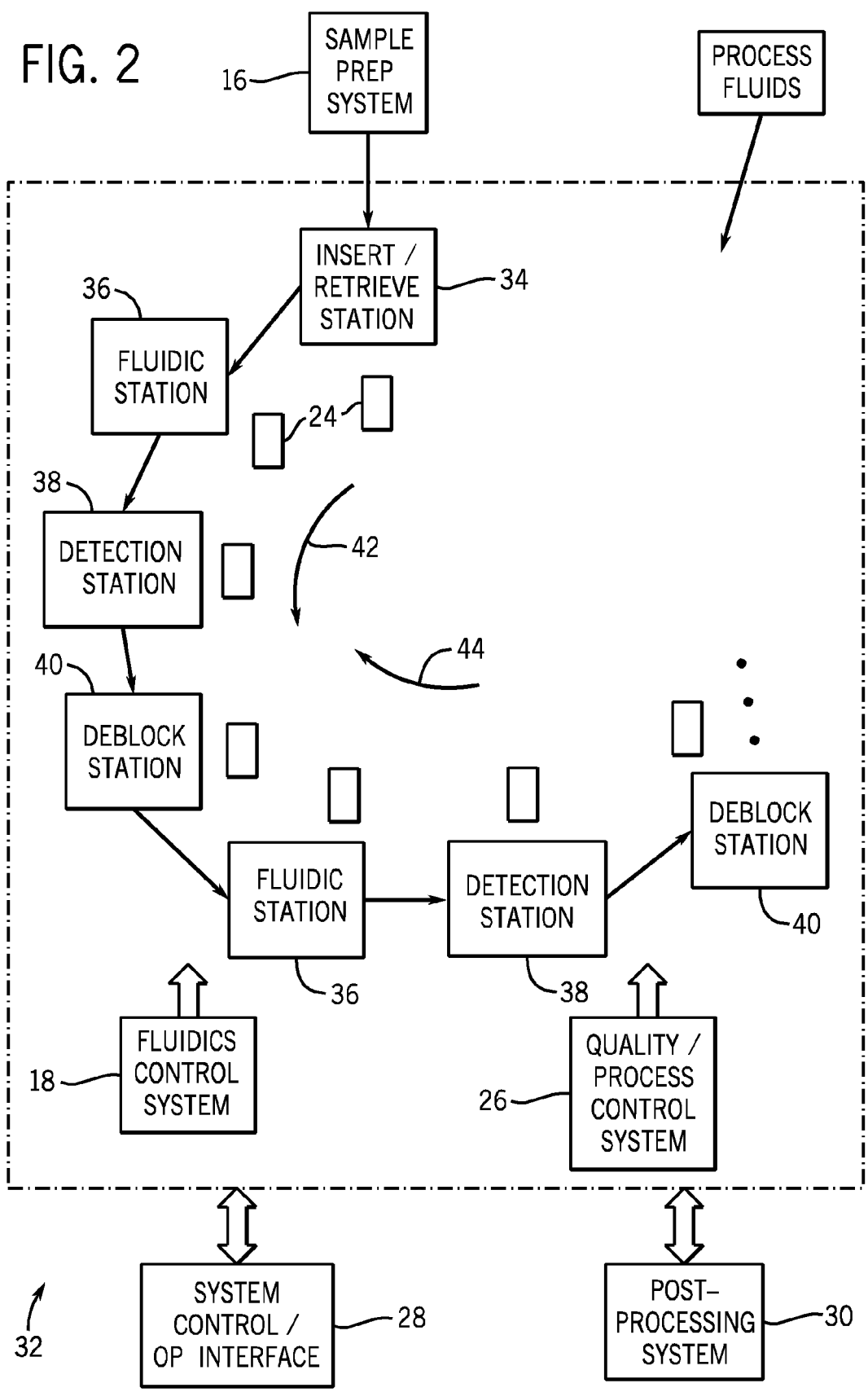
FIG. 2 is a diagrammatical overview of a multi-station sequencing system implementing aspects of the present technique.

The sequencing system 10 may be configured to handle individual samples or may be designed for higher throughput in a manner generally represented in FIG. 2. FIG. 2 illustrates a multi-station sequencer 32 in which multiple stations are provided for the delivery of reagents and other fluids, and for detection of progressively building sequences of nucleotides. In the illustrated embodiment, the sequencer 32 may include a series of stations disposed in a plane, such as on a table, or in multiple planes. To allow samples to be inserted into the sequencer, an insertion/retrieval station 34 will typically be provided. This station will be physically configured to allow a human operator or robot to insert a sample into the device and lodge the sample in a process flow for sequencing operations to be automatically performed at the various additional stations. From the insertion/retrieval station 34, a mechanical conveying system (not illustrated) will serve to move the samples 24 and process between the other stations.

In the embodiment illustrated in FIG. 2, the additional stations will include fluidic stations 36, detection stations 38, and de-blocking stations 40, although other stations may be included or interspersed with these stations depending upon the process and sequence of steps desired. For example, fluidic stations 36 will serve to introduce reagents and other process fluids to the samples 24, such as to allow for binding of individual nucleotides as sequencing progresses. The fluidic stations 36 may also allow for washing or flushing reagents from the samples. Alternatively or additionally, the stage supporting the sample can be configured to allow removal of liquids, including reagents present in the liquids, from samples independent of their location in the system. For example, the stage can include valve actuated vacuum lines that can be activated for removal of liquids from the sample when the sample is at any station or even when the sample is between stations. A useful vacuum system is described, for example, in pending U.S. patent application Ser. No. 11/521,574, which is incorporated herein by reference.

The detection stations 38 may include any desired detection circuitry, such as optical, electrical, or other equipment designed to detect the particular nucleotides added at individual sites of the sample as the sequencing progresses. An exemplary optical system for such detection is described below with reference to FIG. 3. The de-blocking station 40 may be employed for delivering reagents used to remove protective molecules that prevent binding of more than one nucleotide at a time, particularly in SBS systems. The de-blocking station may also be used to cleave fluorescent dyes and similar molecules from the nucleotides or oligo nucleotides as sequencing progresses.

In general, the samples 24 may progress through the sequencer 32 in a progressive flow direction as indicated generally by arrow 42. This may correspond to a normal flow of the sample through the sequencer. However, the samples may retrogress in the stations as indicated generally by reference numeral 44. Such retrogression may be desired to permit re-imaging of the samples, reintroduction of reagents, re-flushing, or generally any repetitive operation that can be performed by a preceding station. It should also be noted that the progression of samples in the system, as also in the system of FIG. 1, may be decoupled in a temporal sense. That is, not all samples need to progress through the stations for the same number of cycles nor do all samples need to enter and exit a multi-cycle process in the same cycle. Samples may be removed from processing, reprocessed, and scheduling of such processing may be altered in real time, particularly where the fluidics control system 18 or the quality/process control system 26 detect that one or more operations was not performed in an optimal or desired manner.

As in the system of FIG. 1, the various stations are coupled to the fluidics control system 18 and to the quality/process control system 26 to permit control of these operations, as well as control of quality of both the samples and of the operations performed at the various processing stations. Moreover, as in the system of FIG. 1, the various stations of the sequencer are linked to a system control/operator interface 28, and data collected is ultimately forwarded to a post-processing system 30 where a sequence data is derived from the detected data, typically image data generated by the detection stations 38.

A system of the invention can be used to continuously sequence nucleic acids in a plurality of different samples. Systems of the invention can be configured to include an arrangement of samples and an arrangement of stations for carrying out sequencing steps. The samples in the arrangement of samples can be placed in a fixed order and at fixed intervals relative to each other. For example, an arrangement of nucleic acid arrays can be placed along the outer edge of a circular table. Similarly, the stations can be placed in a fixed order and at fixed intervals relative to each other. For example, the stations can be placed in a circular arrangement having a perimeter that corresponds to the layout for the arrangement of sample arrays. Each of the stations can be configured to carry out a different manipulation in a sequencing protocol. The two arrangements (i.e. sample arrays and stations) can be moved relative to each other such that the stations carry out desired steps of a reaction scheme at each reaction site. The relative locations of the stations and the schedule for the relative movement can correlate with the order and duration of reaction steps in the sequencing reaction scheme such that once a sample array has completed a cycle of interacting with the full set of stations then a single sequencing reaction cycle is complete. For example, primers that are hybridized to nucleic acid targets on an array can each be extended by addition of a single nucleotide, detected and de-blocked if the order of the stations, spacing between the stations and rate of passage for the array corresponds to the order of reagent delivery and reaction time for a complete sequencing reaction cycle.

In accordance with the configuration set forth above, and described in further detail below, each lap (or full revolution in embodiments where a circular table is used) completed by an individual sample array can correspond to determination of a single nucleotide for each of the target nucleic acids on the array. Furthermore, several sample arrays present in the system (for example, on the circular table) concurrently move along similar, repeated laps through the system, thereby resulting in continuous sequencing by the system. Using a system or method of the invention, reagents can be actively delivered or removed from a first sample array in accordance with a first reaction step of a sequencing cycle while incubation, or some other reaction step in the cycle, occurs for a second sample array. Thus, a set of stations can be configured in a spatial and temporal relationship with an arrangement of sample arrays such that reactions occur at multiple sample arrays concurrently even as the sample arrays are subjected to different steps of the sequencing cycle at any given time, thereby allowing continuous and simultaneous sequencing to be performed.

Embodiments of the invention provide a system that is configured to allow replacement of a first sample array with a second sample array while the system continuously sequences nucleic acids of a third sample array. Thus, a first sample array can be individually added or removed from the system without interrupting sequencing reactions occurring at another sample array, thereby providing the advantage of continuous sequencing for the set of sample arrays. A further advantage is that sequencing runs of different lengths can be performed continuously and simultaneously in the system because individual sample arrays can complete a different number of laps through the system and the sample arrays can be removed or added to the system in an independent fashion such that reactions occurring at other sites are not perturbed.

Figure 3:
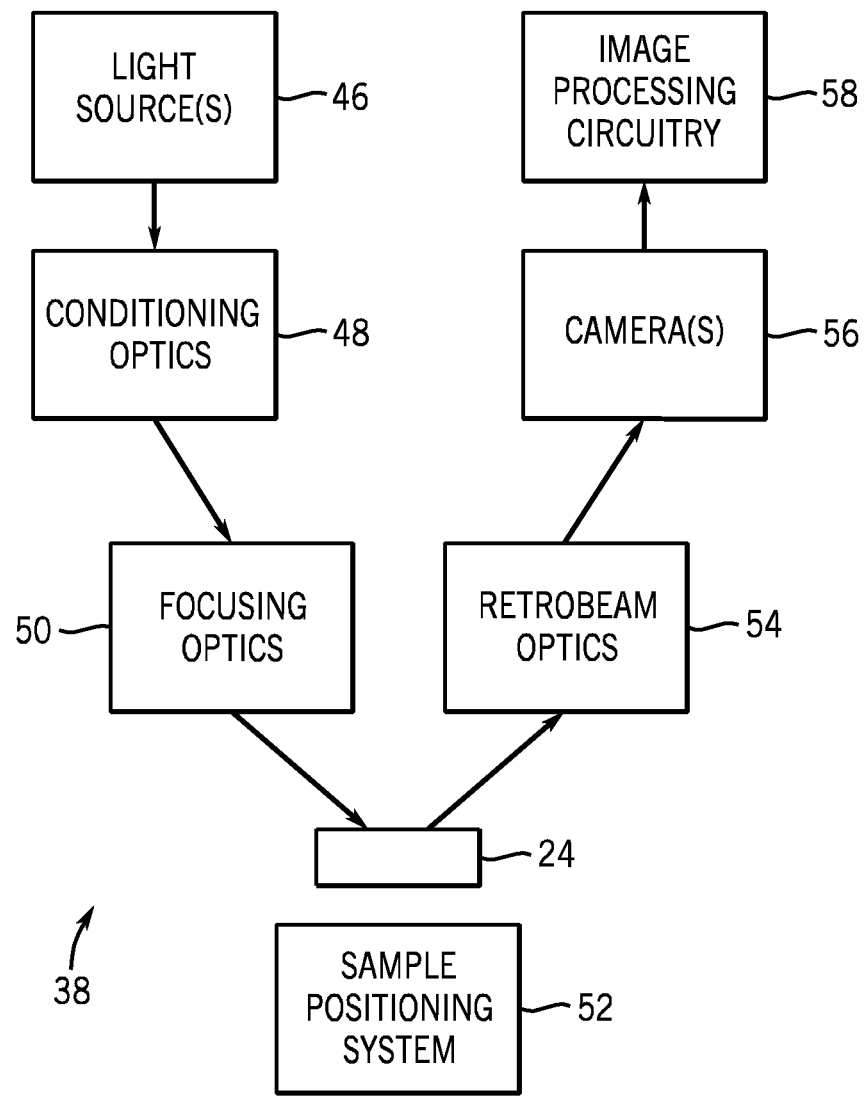
FIG. 3 is a diagrammatical overview of an exemplary imaging system that may be used in conjunction with the system of FIG. 1 or 2 for detection of sequences at individual sites in an array.

FIG. 3 illustrates an exemplary detection station 38 designed to detect nucleotides added at sites of an array in accordance with a presently contemplated optical system. As set forth above, a sample may be moved to two or more stations of the device that are located in physically different locations or alternatively one or more steps can be carried out on a sample that is in communication with the one or more stations without necessarily being moved to different locations. Accordingly, the description herein with regard to particular stations is understood to relate to stations in a variety of configurations whether or not the sample moves between stations, the stations move to the sample, or the stations and sample are static with respect to each other. In the embodiment illustrated in FIG. 3, one or more light sources 46 provide light beams that are directed to conditioning optics 48. The light sources 46 may include one or more lasers, with multiple lasers typically being used for detecting dyes that fluoresce at different corresponding wavelengths. The light sources may direct beams to the conditioning optics 48 for filtering and shaping of the beams in the conditioning optics. For example, in a presently contemplated embodiment, the conditioning optics 48 combine beams from multiple lasers and generate a generally linear beam of radiation that is conveyed to focusing optics 50.

The sample 24 is positioned on a sample positioning system 52 that may appropriately position the sample in three dimensions, and may displace the sample for progressive imaging of sites on the sample array. In a presently contemplated embodiment, the focusing optics 50 confocally direct radiation to one or more surfaces of the array at which individual sites are located that are to be sequenced. Depending upon the wavelengths of light in the focused beam, then, a retrobeam of radiation is returned from the sample due to fluorescence of dyes binded to the nucleotides at each site.

The retrobeam is then returned through retrobeam optics 54 which may filter the beam, such as to separate different wavelengths in the beam, and direct these separated beams to one or more cameras 56. The cameras 56 may be based upon any suitable technology, such as including charge coupled devices that generate pixilated image data based upon photons impacting locations in the devices. The cameras generate image data that is then forwarded to image processing circuitry 58. In general, the processing circuitry 58 may perform various operations, such as analog-to-digital conversion, scaling, filtering, and association of the data in multiple frames to appropriately and accurately image multiple sites at specific locations on the sample. The image processing circuitry 58 may store the image data, and will ultimately forward the image data to the post-processing system 30 where sequence data can be derived from the image data. Particularly useful detection devices that can be used at a detection station include, for example, those described in US 2007/0114362 (U.S. patent application Ser. No. 11/286,309) and WO 07/123744, each of which are incorporated herein by reference.

Figure 4:
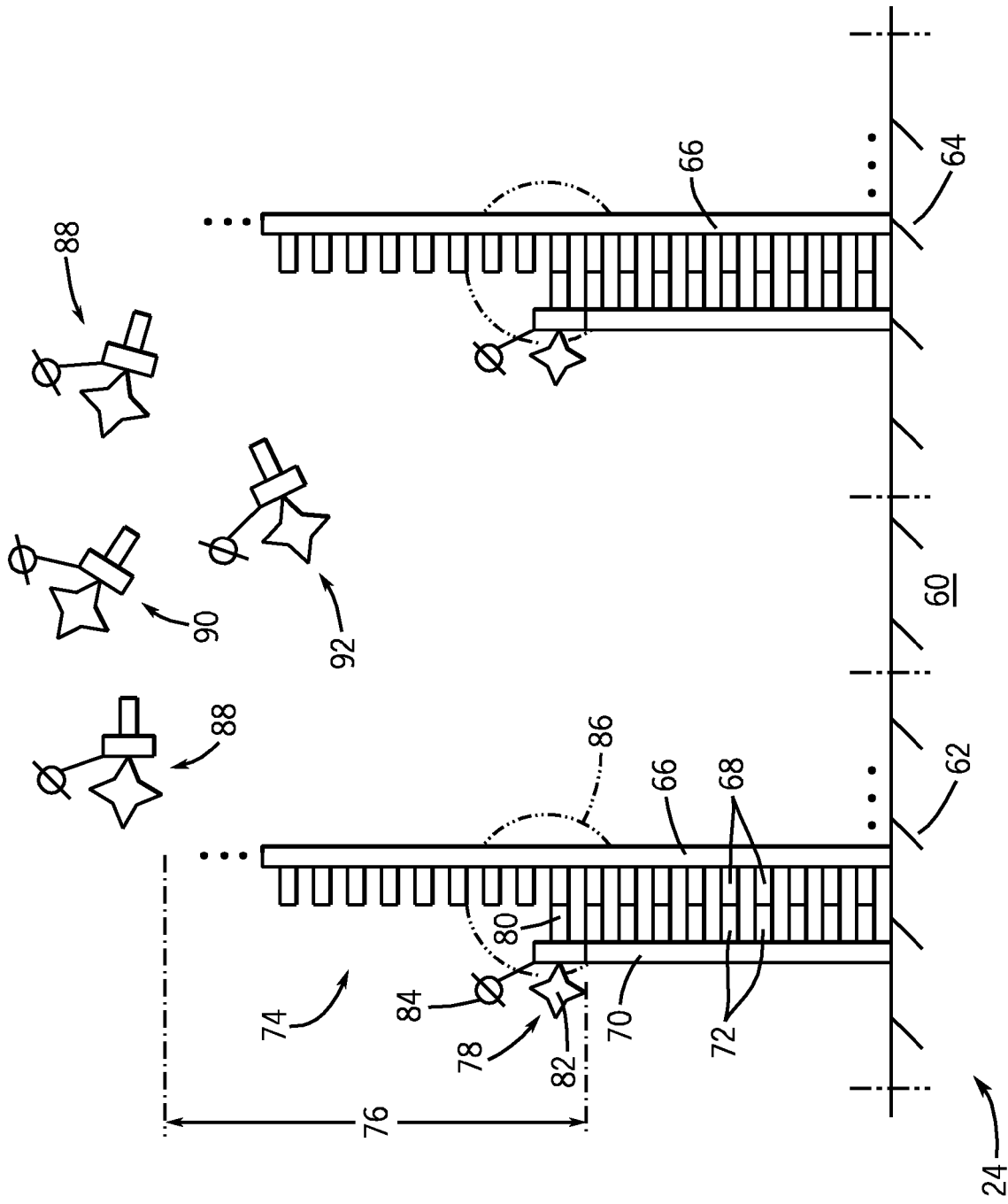
FIG. 4 is a diagrammatical representation of sequencing in the systems of the preceding figures in accordance with an SBS technique, as one example of the sequencing approach that may be used in the systems.

FIG. 4 illustrates a typical reaction cycle in a sequencing by synthesis technique for oligonucleotides that may benefit from the nucleotide recapture and recycling technique of the present invention. In general, the synthesis operation summarized in FIG. 4 may be performed on a sample 24 comprising a support 60 on which a multitude of sites 62 and 64 are formed. In the preparation of each sample 24, many such sites may be formed, each with unique fragments of genetic material as indicated generally by reference numeral 66. These fragments may constitute templates of DNA or RNA to be sequenced. The fragments can be isolated from a biological source using methods known in the art. In embodiments utilizing amplification methods, the fragments can be amplicons of a DNA or RNA isolated from a biological source. Each template comprises a number of mers or bases 68 which will uniquely bind to a complimentary nucleotide (or analog thereof) during the synthesis process. The sequencing process begins with binding of an anchor primer 70 to each of the templates. This anchor primer includes complimentary bases 72 that bind with those of a corresponding sequence of the template. The remaining portion of the template, designated generally by reference numeral 74, constitutes that portion to be sequenced. The length 76 of this portion may vary, with presently contemplated embodiments extending from 25 to 40 bases or more.

As sequencing progresses, the introduced processed stream will include all four common DNA nucleotides, one of which will add to the primer at a position that is opposite the next available base in the template, as indicated by reference numeral 78. The added nucleotide will include a base 80 that is complementary to the template as well as a fluorescent tag 82 and a blocking molecule 84. As will be noted by those skilled in the art, as used herein, the term "nucleotides" in the illustrated processes will typically include units from which DNA molecules are constructed. Although any nucleotides or oligonucleotides may be recaptured and recycled in accordance with the present technique, in many practical applications, these will include deoxynucleotide-triphosphates (dNTP), each carrying a single nitrogenous base (adenine, guanine, cytosine or thymine). The complimentary nucleotide is added to the primer due to the activity of a polymerase, as indicated generally by reference numeral 86. Other nucleotides than the specific one binding to the template will also be present in the process fluid, as indicated generally by reference numerals 88, 90 and 92 in FIG. 4. Nucleotides not binding to the templates will subsequently be washed from the sample in a flushing operation, exiting in the effluent stream to be recaptured and recycled as described above.

The sequencing system utilized of the type described above for analysis of oligonucleotide sequences may be automated and regulated in a number of ways. In general, the performance and quality control implemented by the present invention may allow for normal sequencing operations on one or many sample arrays, which may be altered based upon detected issues with performance or quality of the sample array, performance of the fluidics control/delivery system, performance of the detection system, or any subcomponent or subsystem of these. When exceptions or anomalies in quality or performance are detected, remedial measures may be taken to correct the system performance, re-sequence or rerun certain sequencing cycle steps, such as nucleotide addition, imaging, de-blocking and so forth, or even interrupt sequencing altogether. Because the sequencing will represent an investment in terms of time and materials, the remedial measures may be adapted to continue sequencing if at all possible, while taking steps to guard against pursuing a synthesis procedure that is destined to fail or at least destined to produce results that are not of sufficient value to warrant the time and materials spent. Thus, remedial measures may improve the likelihood that reliable sequencing data will be obtained.

Masking methods and apparatus will be exemplified below with regard to a sequencing device and method of the type set forth above. However, the masking can be used to process image data from any of a variety of situations where images are repeatedly obtained from an object and the images include areas of the object having desired information along with areas having undesirable information content. In such situations where the areas of desired information are to be compared between images or in some way analyzed together and the undesirable information is captured in the initial image, the masking methods can be useful to remove the undesirable information to reduce the amount of computer storage space or valuable processing activity required to evaluate the object. The masking methods and apparatus are particularly useful for objects in which the desired information areas occur in a random pattern or a complex pattern such as one that is difficult to predict or define prior to obtaining an image. However, in cases where the information occurs in an ordered predictable pattern the masking methods are also useful.

As noted above, the cyclic imaging of the sample array for sequencing may generate vast quantities of image data, particularly insomuch as multiple cycles of imaging of multiple samples may be performed, depending upon the length of the polymer to be sequenced. For example, presently contemplated embodiments may permit for sequencing of at least 25 to 40 mers. The high resolution imaging performed, with progressive scans of the sample at multiple sites, in combination with the digital depth of the pixel information results in very considerable quantities of data, a large portion of which may not actually correspond to locations of sites in the array of the sample. In accordance with the present invention, a mask may be utilized to reduce the processing of such regions of little interest, as well as the memory required during sequencing for storing image data for such areas.

Figure 5:
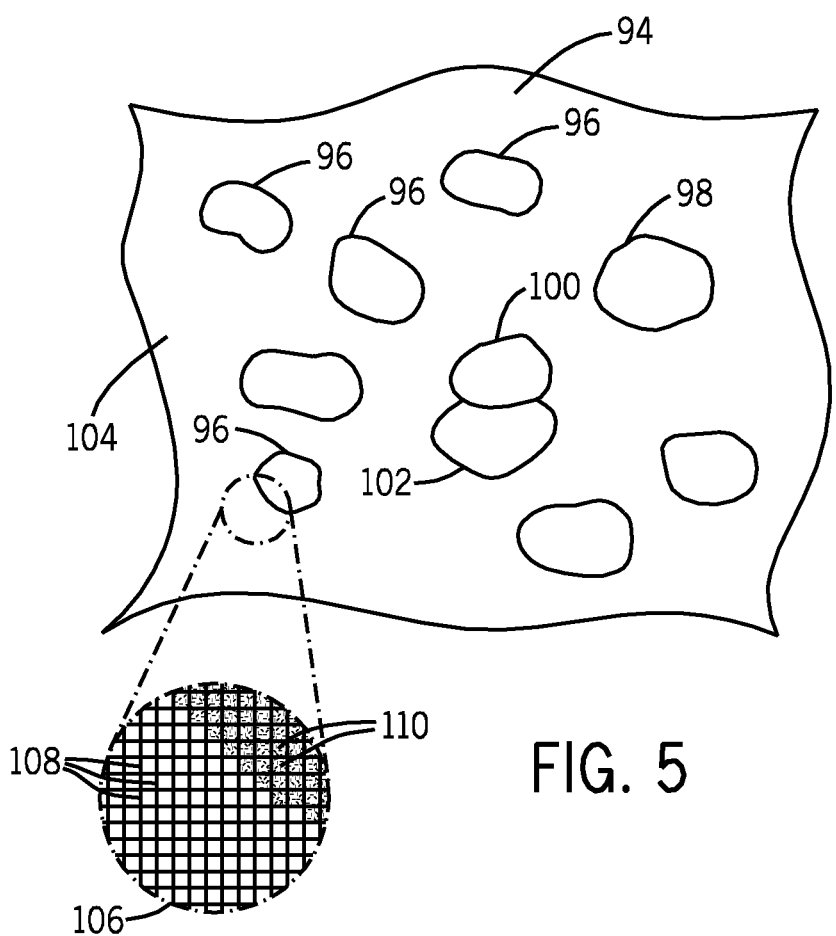
FIG. 5 is a simplified top view of a portion of an array of sites of nucleic acids to be sequenced.

To illustrate this technique, FIG. 5 shows a portion of a sample array, designated generally by reference numeral 94. In the illustrated example, individual sites 96 of genetic material to be sequenced are dispersed on a surface of the array. It should be noted that in the illustrated embodiment, these sites are somewhat randomly or at least non-uniformly positioned on the array. In practice, these sites may be non-uniformly positioned, or may be located in a geometric grid pattern on the array. In the illustrated embodiment, multiple sites 96 are present, which may have varying shapes and sizes, typically depending upon the manner in which the sample is prepared.

Additional sites 98 may be provided as "control" sites. These sites may include known sequences, such as repeating sequences of nucleotides in an oligonucleotide template, or a homopolymer oligonucleotide comprising a single common nucleotide type only. Such control sites may be employed for monitoring the efficiency of the sequencing operation as sequencing progresses. It should also be noted in FIG. 5 that certain of the sites may be closely adjacent to one another as indicated by sites 100 and 102. If desired, sites that are believed to be too close to allow accurate sequencing can be masked, thereby removing them from subsequent image analysis. Close sites and other sites for which further image analysis is not desired can be masked using method set forth herein in regard to masking regions that lack sites of interest. The present technique also facilitates using information for such sites as sequencing progresses, rather than discarding such information due to possible confusion between the sites.

In many arrays, large regions 104 will not include sites of interest to be analyzed for sequencing data. As described below, these regions 104 may be masked in the processing of the image data to enhance computational efficiency and reduce memory allocated for the image data corresponding to these regions.

As illustrated in FIG. 5, an image data for the portion 94 of the array will comprise a pixilated grid 106 in which individual picture elements or pixels 108 may be visible. In practice, an actual visual image of the array may or may not be generated, but pixilated data is nevertheless collected for processing and analysis. Pixels 108 for regions 104 that do not contain sites of interest for analysis may generally provide a substantially uniform background (e.g., dark). By contrast, pixels 110 corresponding to the locations of sites of interest 96 will include data representative of grey scales, color, or some other quality indicative of the presence and nature of the site. In presently contemplated embodiments, for example, such pixel data will denote a unique color corresponding to dye for different individual nucleotides.

Figure 6:
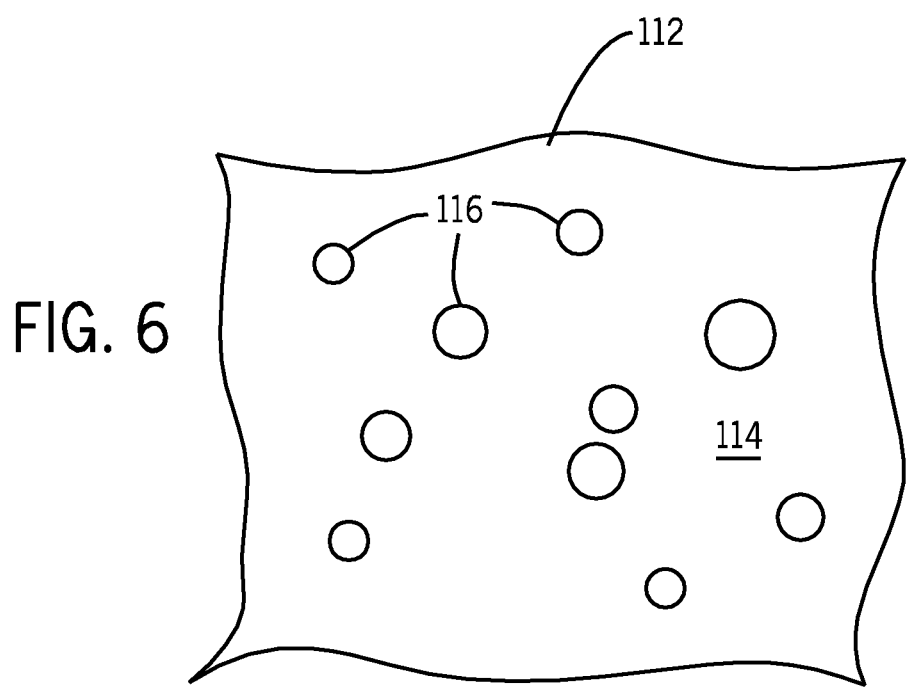
FIG. 6 is a diagrammatical representation of a digital mask that corresponds to the segment of the array illustrated in FIG. 5.

To enhance computational efficiency and reduce memory utilization during the sequencing processes, the present technique calls for establishing a digital mask of the sites of interest and other regions where no sites of interest exist. For example, FIG. 6 illustrates a portion of a digital mask corresponding to the portion 94 of the array illustrated in FIG. 5. The mask 112, which will typically take the form of a look-up table or other data structure, provides for referenced addresses of individual pixels, and values for the pixels, the values denoting whether the pixel location corresponds to a site of interest or not. Regions 114 in the mask, for example, may be given a first value, such as "0", while other regions 116 corresponding to pixel locations where sites of interest are located may be given a second value, such as "1". As image data is collected, then, the referenced locations are compared to the mask 112, and data corresponding to the sites is processed differently from data corresponding to the masked region 114. In a present embodiment, for example, the pixel data for the masked region may be discarded (e.g., deleted), and only pixel data for the sites of interest stored, processed and utilized in deriving sequence data. It should also be noted that the mask 112 may map sites 116 to reduce outlying areas of each site which may otherwise confuse or reduce the efficiency of sequencing recognition. This may be particularly useful for closely adjacent sites such as sites 100 and 102 illustrated in FIG. 5.

It should be noted that the masks utilized in the present technique, which may be referred to as "pixel masks" or "digital masks" or "binary masks" may be determined and utilized in several ways. For example, an actual bit mask may be developed based upon digitized image data. However, more efficient masking may include establishing of an addressed mask for regions, such as at a pixel level. Such pixel-by-pixel masks may address specific pixels in image data and indicate whether such pixels are to be processed as sites for sequencing, or as regions of little or no interest (e.g., not sequenced or processed differently from pixels addressed as sites). Still further, regions comprising multiple pixels may be addressed, such as by reference to their coordinates in the array, their size, shape, and so forth. Such regions may be those that are masked for processing as sites, or the contrary. In a practical implementation, a binary mask will effectively encode both. That is, based upon the addresses of particular regions, the mask will make clear whether the image data for the region is of interest for sequencing or not.

Figure 7:
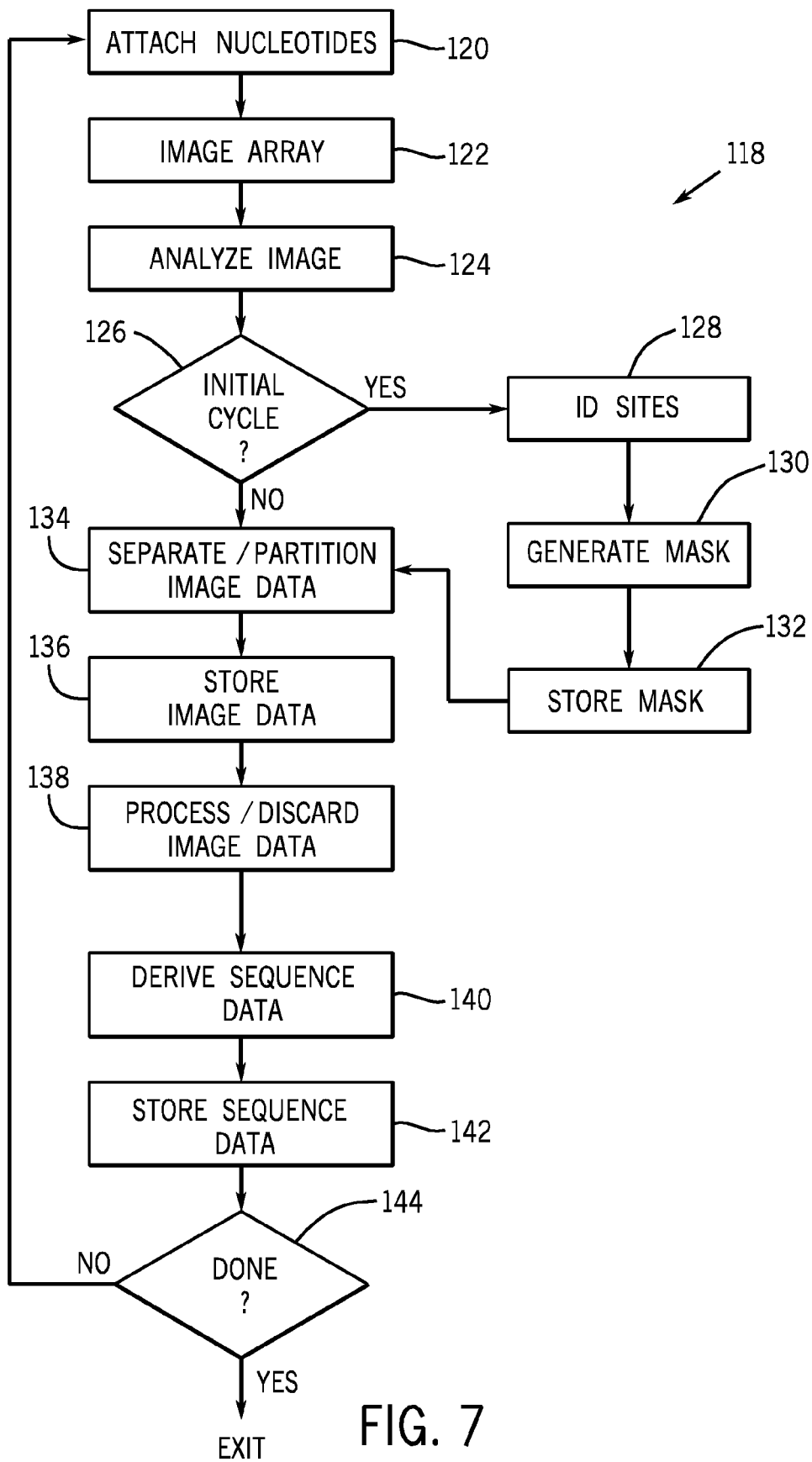
FIG. 7 is a flow chart illustrating exemplary logic in the treatment of image data for generation and use of the mask for sequencing.

FIG. 7 is a flow chart illustrating exemplary logic for carrying out the masking approach in a sequencing operation. The logic, designated globally by reference numeral 118 begins with a first cycle of attachment of nucleotides to individual templates at the sites to be sequenced, as indicated by step 120. At step 122, then, the array is imaged, and at step 124 the image data is analyzed. In a presently contemplated embodiment, the mask is derived from an image obtained during a first cycle through the sequencing process. Because the first cycle will result in a retrobeam that includes information for the sites of interest, the sites may be located and registered by reference to the image data analyzed at step 124.

Thus, at step 126 the logic determines whether the current cycle is the initial cycle of sequencing. If so, the logic proceeds to step 128 where the sites of interest are identified by reference to the image data. For example, a relatively uniform background color or intensity will be anticipated for regions not corresponding to sites of interest, while the sites of interest will be recognizable by image data encoding received light of substantially different wavelengths, color, intensity, or another image characteristic. At step 130 the digital mask is generated, which may be a binary mask as described above. The mask will reference individual pixel locations in the array and attribute values to sites of interest, with different values being attributed to regions of little or no interest. At step 132 the mask is stored, such as in the form of a lookup table or other digital map.

The logic of FIG. 7 then progresses to step 134 where the image data for sites of interest is separated or partitioned from image data for masked regions not of interest in sequencing. At step 136, then, the image data for the sites is stored. This step may include various image processing that may filter or analyze the image data, such as for quality control. The data not corresponding to the locations of sites of interest is otherwise processed, and, as indicated by optional logical step 138, may be discarded. It should also be noted that the logic may call for storing some or all of the image data for masked (non-site) regions for at least one cycle through the sequencing routine, such as for quality control, comparison purposes, and so forth.

At step 140 sequence data is derived from the image data. Step 140 may be performed in a generally known manner, such as by recognition of particular colors corresponding to dyes attached to different nucleotide types. At step 142, then, the sequence data is stored for subsequent processing. It should be noted that sequencing of the sample performed at steps 140 and 142 may be completely divorced from the imaging process, and performed in subsequent post-processing based upon stored image data for the sites of interest.

At step 144, then, it is determined whether sequencing is complete, and if not the logic returns to step 120 for another cycle. In subsequent cycles of sequencing, then, the mask stored at step 132 will be employed to filter the image data so as to process only image data for the sites of interest for sequencing purposes.

Figure 8:
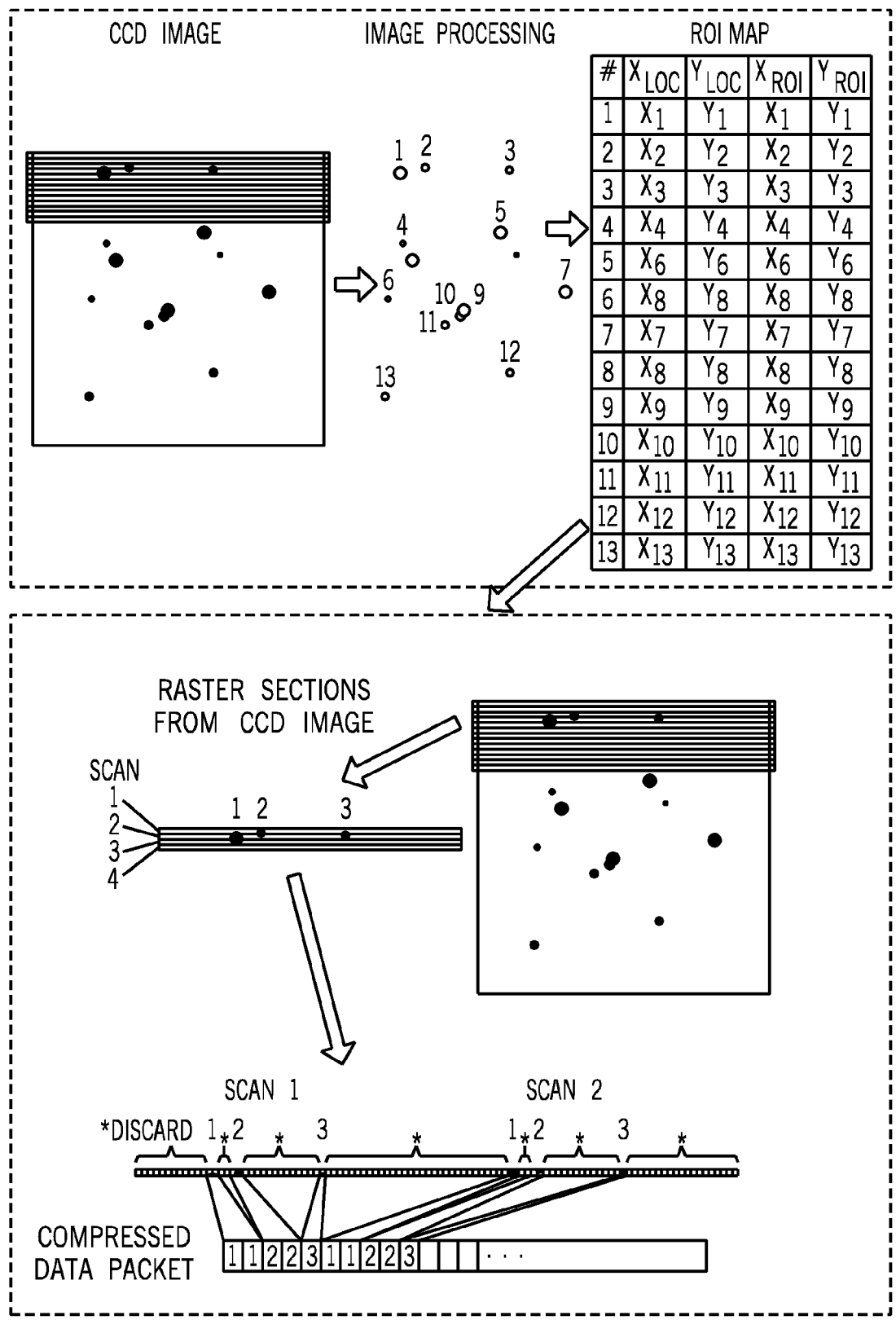
FIG. 8 is a diagrammatical representation of an exemplary masking method.

A diagrammatical representation of an exemplary masking method is provided in FIG. 8. The section enclosed by the upper dashed box is a diagrammatic representation of steps of the process in which the mask is generated. The image labeled as "CCD image" in the upper box is a random array, wherein features of the array containing nucleic acids to be sequenced are visible as white spots on the black background. The CCD array is overlaid with grey bars indicating areas imaged by successive raster scans. The image labeled "Image Processing" shows a representation of the desired information content from the CCD image in which the relative spatial locations of the features is retained, the features are numbered and the unwanted black space in the CCD image is absent. The ROI map shows a lookup table in which each feature from the CCD image is identified by its X and Y coordinates ($X_{LOC}$ and $Y_{LOC}$, respectively), and boundaries approximated by a square having dimensions in the X/Y coordinate system represented by $X_{ROI}$ and $Y_{ROI}$, respectively.

The section of FIG. 8 enclosed by the lower dashed box is a diagrammatical representation of steps for applying the mask to subsequent images. A subsequent CCD image is shown in the upper right corner of the lower dashed box along with four raster sections from the CCD image (identified as scan 1, 2, 3, and 4). As shown in the diagram, the raster sections encompass three features. Two of the raster scans are shown in the lower portion of the box along with a compressed data packet derived from the scans by applying the digital mask derived from the first CCD image.

In some applications of the masking methods, each feature will have unique characteristics that are detected in separate imaging steps. For example, in sequencing-by-synthesis applications different sequences will typically be present at each feature and the sequencing method may be typically carried out by stepwise addition of a single species of labeled nucleotide followed by imaging. Thus, it may require four nucleotide addition and imaging steps before all of the features are detected. It will typically be the case that no single CCD image shows all of the features (since it is likely that at any given step only about 25% of the features will be detected by the particular nucleotide being added). In such cases it is possible to create the mask using information from more than one image. For example, in a sequencing application in which four different labeled nucleotides are added in sequential steps, it is useful to create the mask from the four different images captured after addition of the four different labeled nucleotides. This may not be necessary if the sequencing primers and their priming binding sites are constructed such that the same base is added to every feature in the first step. Alternatively, a mixture of all four bases can be added in a first step for purposes of creating the mask and reading of the sequence may commence with the addition of nucleotides at the second position of the sequence at each feature.

Figure 9:
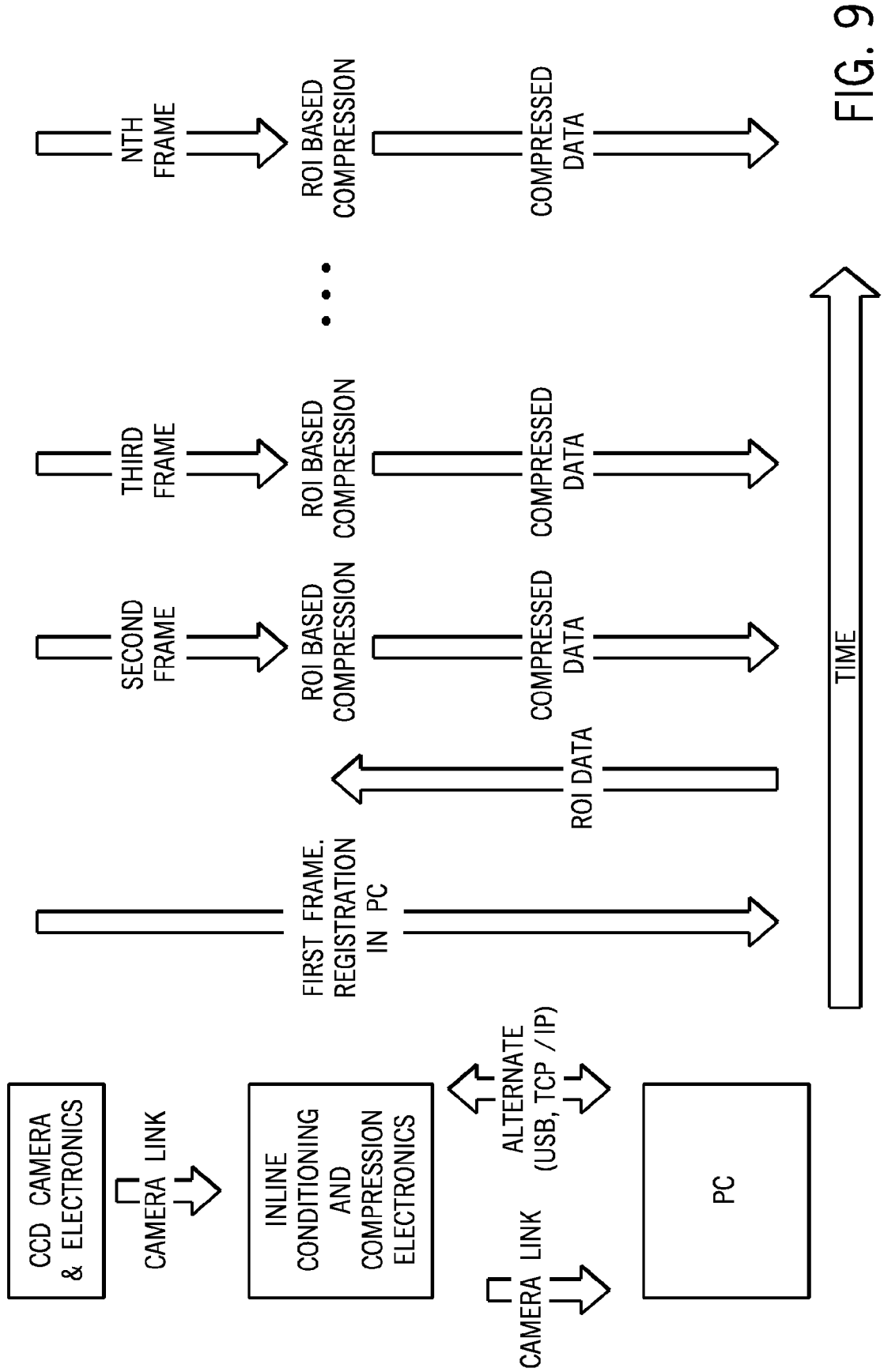
FIG. 9 is a diagrammatical representation of an exemplary system for carrying out a masking method.

FIG. 9 shows a diagrammatical representation of an exemplary system for carrying out a masking method. The system includes a CCD camera along with electronics necessary to obtain images. The camera is linked to inline conditioning and compression electronics which are linked to a computer (for example, a personal computer (PC)). The PC may be configured to communicate with the inline conditioning and compression electronics, for example, via alternate USB and TCP/IP communications. As shown by the arrows in FIG. 9, the system works as follows. The CCD integrates and passes on an initial image. This image is passed through the compression stage unchanged to the PC interface. Normal registration is performed on the image by the PC software. Features of interest are identified and mapped in an ROI table. The ROI table is sent to the compression electronics. Subsequent image data is parsed according to the ROI map and compressed into data packets. These packets are passed into the PC.

It may be beneficial in some embodiments to size the ROI some predetermined amount larger than the feature. This can improve registration and robustness of the parsing and processing versus movement of the image relative to the camera. The larger ROI will typically be selected to accommodate shifting around the feature within the ROI for different images. The oversizing can be maintained in the ROI map and will affect the scan line level processing, i.e. the compression electronics will likely be dealing with more than one scan line at a time in order to deal with an ROI that is shifted due to a shift of the features relative to the camera (and the original ROI map) when the frame is captured. Shifts of ROI along a scan can be dealt with at the scan level. After processing the first few scan lines in a frame, the system will typically be able to determine the overall amount of shift of registration (X, Y, and theta for the particular frame) and update the ROI map with data for use with that frame. This may happen for each new frame.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for sequencing a plurality of nucleic acids, comprising:
   (a) performing a cycle of a sequencing procedure for an array comprising a plurality of nucleic acids at sites of interest on the array;
   (b) imaging the array to generate image data;
   (c) analyzing the image data to identify locations of the sites of interest on the array;
   (d) generating a mask based upon the locations of the sites of interest on the array, wherein the mask corresponds to a plurality of sites of interest for which image data acquired during subsequent cycles of the sequencing procedure is filtered; and
   (e) processing the image data based upon the mask to derive sequence data from the image data, the sequence data indicative of nucleotide species present at the sites of interest on the array;
   wherein steps (a), (b) and (e) are repeated, and wherein in subsequent repetitions of step (e), image data corresponding to locations of the sites of interest is processed differently from image data corresponding to other locations as defined by the mask.

2. The method of claim 1, wherein image data not corresponding to the sites of interest as defined by the mask is discarded during the processing.

3. The method of claim 1, wherein image data not corresponding to the sites of interest as defined by the mask is discarded prior to the processing.

4. The method of claim 1, wherein image data not corresponding to the sites of interest as defined by the mask is not analyzed to derive sequence data.

5. The method of claim 1, wherein the cycle of the sequencing procedure includes disposing optically detectable markers at the sites of interest.

6. The method of claim 1, wherein the sequencing procedure is based upon hybridization of templates at the sites of interest.

7. The method of claim 1, wherein the mask is a binary mask in which pixel locations corresponding to the sites of interest are attributed a first value and other pixel locations are attributed a second value.

8. The method of claim 1, wherein the sites are located in a non-uniform distribution on the array.

9. The method of claim 1, wherein the mask comprises a lookup table identifying coordinates for the sites of interest in the image.

10. The method of claim 9, wherein the lookup table further comprises an approximation of the region of interest (ROI) for the sites of interest.

11. The method of claim 9, wherein in subsequent repetitions of step (e) a second image is compressed into data packets to derive sequence data from the second image.

12. A method for sequencing a plurality of nucleic acids, comprising:
   (a) performing a cycle of a sequencing procedure for an array comprising a plurality of nucleic acids via a system capable of determining nucleotide sequence of the array;
   (b) evaluating a parameter of the system indicative of system performance;
   (c) altering the sequencing procedure for the array based on the parameter;
   (d) imaging the array to generate image data;
   (e) analyzing the image data to identify locations of sites of interest on the array;
   (f) generating a mask based upon the locations of the sites of interest on the array, wherein the mask corresponds to a plurality of sites of interest for which image data acquired during subsequent cycles of the sequencing procedure is filtered; and
   (g) processing the image data based upon the mask to derive sequence data from the image data, the sequence data indicative of nucleotide species present at the sites of interest on the array;
   wherein steps (a)-(d) and (g) are repeated, and wherein in subsequent repetitions of step (g), image data corresponding to locations of the sites of interest is processed differently from image data corresponding to other locations as defined by the mask.

13. The method of claim 12, wherein the parameter relates to a quality of the array.

14. The method of claim 12, wherein the parameter relates to performance of a fluidics control and delivery system.

15. The method of claim 12, wherein the parameter relates to performance of a detection system.

16. The method of claim 12, wherein step (c) includes repeating introduction of nucleotides to the array.

17. The method of claim 12, wherein step (c) includes re-imaging the array.

18. The method of claim 12, wherein step (c) includes repeating a de-blocking operation.

19. A sequencing system, comprising:
   (a) a camera configured to capture a first image of an array and a second image of the array, wherein the array comprises a plurality of nucleic acids at sites of interest on the array;
   (b) a computer having instructions for processing the first image of the array to create a mask, wherein the mask preferentially selects signals from the sites of interest on the array, and wherein the mask corresponds to a plurality of sites of interest for which image data acquired during subsequent cycles of a sequencing procedure is filtered, and wherein the computer is configured to process the unfiltered image data acquired during subsequent cycles of the sequencing procedure differently than filtered image data; and
   (c) a data compression device configured to convert the second image to a compressed data packet based on the mask, wherein the compressed data packet comprises signals from the sites of interest on the array, wherein the computer is further configured to process the signals from the sites of interest on the array in the compressed data packet to derive sequence data for the nucleic acids at the sites of interest on the array.

20. The sequencing system of claim 19, wherein the system is configured to discard data from the second image that does not include signals from the sites of interest.

21. The sequencing system of claim 20, wherein the data compression device is a separate component from the computer such that the second image is not stored in the memory of the computer.

22. The sequencing system of claim 19, wherein the mask comprises a lookup table identifying coordinates for the sites of interest in the image.

23. The sequencing system of claim 22, wherein the lookup table further comprises an approximation of the region of interest (ROI) for the sites of interest.

24. The sequencing system of claim 22, wherein the system is configured to convert a plurality of images to data packets based on the mask.

25. A method for sequencing a plurality of nucleic acids, comprising:
   (a) performing a cycle of a sequencing procedure for an array comprising a plurality of nucleic acids at sites of interest on the array;
   (b) imaging the array to generate image data;
   (c) analyzing the image data to identify locations of the sites of interest on the array;
   (d) generating a mask based upon the locations of the sites of interest on the array; and
   (e) processing the image data based upon the mask to derive sequence data from the image data, the sequence data indicative of nucleotide species present at the sites of interest on the array, wherein image data not corresponding to the sites of interest on the array as defined by the mask is discarded prior to the processing;
   wherein steps (a), (b) and (e) are repeated, and wherein in subsequent repetitions of step (e), image data corresponding to locations of the sites of interest is processed differently from image data corresponding to other locations as defined by the mask.

26. The method of claim 1, wherein the mask is generated using information from more than one image, wherein each image corresponds to a different labeled nucleotide.

27. The method of claim 26, wherein the mask is generated using information from a plurality of images, and wherein no single image in the plurality of images shows all of the sites of interest.

28. The method of claim 12, wherein the mask is generated using information from a plurality of images, and wherein no single image in the plurality of images shows all of the sites of interest.

29. The sequencing system of claim 19, wherein the computer includes instructions for processing a plurality of images to create the mask, wherein no single image in the plurality of images shows all of the sites of interest.

30. The method of claim 25, wherein the mask is generated using information from a plurality of images, and wherein no single image in the plurality of images shows all of the sites of interest.

* * * * *